(12) United States Patent
Nobles et al.

(10) Patent No.: US 6,171,319 B1
(45) Date of Patent: Jan. 9, 2001

(54) ANASTOMOSIS DEVICE WITH HOLE PUNCH

(75) Inventors: Anthony A. Nobles, Fountain Valley; Naoum A. Baladi, Redwood City, both of CA (US)

(73) Assignee: Cardio Medical Solutions, Inc., Santa Ana, CA (US)

( * ) Notice: Under 35 U.S.C. 154(b), the term of this patent shall be extended for 0 days.

(21) Appl. No.: 09/300,187

(22) Filed: Apr. 27, 1999

Related U.S. Application Data

(62) Division of application No. 09/036,125, filed on Mar. 6, 1998, now Pat. No. 5,944,730.
(60) Provisional application No. 60/046,972, filed on May 19, 1997.

(51) Int. Cl.$^7$ .................................................. A61B 17/08
(52) U.S. Cl. ............................................ 606/151; 606/194
(58) Field of Search .................................. 606/151, 198, 606/213, 200, 190, 191, 194, 158; 604/104–107, 127

(56) References Cited

U.S. PATENT DOCUMENTS

| | | |
|---|---|---|
| 4,744,364 | 5/1988 | Kensey . |
| 4,774,091 | 9/1988 | Yamahira et al. . |
| 4,794,928 | 1/1989 | Kletschka . |
| 5,122,122 * | 6/1992 | Allgood ................................ 604/174 |
| 5,192,301 | 3/1993 | Kamiya et al. . |
| 5,222,974 | 6/1993 | Kensey et al. . |
| 5,290,249 * | 3/1994 | Foster et al. ......................... 604/174 |
| 5,330,446 | 7/1994 | Weldon et al. . |
| 5,330,497 * | 7/1994 | Freitas et al. ........................ 606/185 |
| 5,342,393 | 8/1994 | Stack . |
| 5,350,399 | 9/1994 | Erlebacher et al. . |
| 5,370,685 * | 12/1994 | Stevens .................................... 623/2 |
| 5,383,896 | 1/1995 | Gershoney et al. . |
| 5,395,383 * | 3/1995 | Adams et al. ........................ 606/151 |
| 5,447,515 | 9/1995 | Robicsek . |
| 5,496,332 | 3/1996 | Sierra et al. . |
| 5,527,338 | 6/1996 | Purdy . |

(List continued on next page.)

Primary Examiner—Michael Buiz
Assistant Examiner—Jonathan D. Goldberg
(74) Attorney, Agent, or Firm—Knobbe, Martens, Olson & Bear, LLP

(57) ABSTRACT

The present invention provides a device and method for creating a seal around the inner wall of an incision in a blood vessel. The device is particularly adapted to create an anastomosis site for coronary artery bypass grafts to a patient's aorta without obstructing the flow of blood in the aorta. The device comprises an extruded tube with a translatable shaft positioned therein. One end of the shaft is coupled to a handle of the device which allows a practitioner to advance and withdraw the shaft relative to the tube. The other end of the shaft is connected to a flexible inverting member which is attached to the distal end of the tube. By manipulating the handle, the practitioner can remotely deform the inverting member between two configurations: an elongated, narrow configuration in which the inverting member is adapted to be inserted through a small incision, and an inverted configuration in which the inverting member forms an expanded, inward-facing cup. In operation, the medical practitioner inserts the inverting member into the blood vessel through an incision while the inverting member is maintained in its elongated, narrow configuration, and then manipulates the handle to cause the inverting member to assume its inverted configuration. A seal is then formed by applying a proximal force to the device to cause a rim of the cup to form a seal against an inner wall of the blood vessel. This prevents blood from flowing out of the incision and creates a working area for performing an end-to-side anastomosis. The working area is formed without interrupting the flow of blood through the vessel. The device preferably includes a hole punch device slidably mounted to the tube for allowing the practitioner to create an anastomosis hole once the seal has been formed.

32 Claims, 16 Drawing Sheets

U.S. PATENT DOCUMENTS

| | | |
|---|---|---|
| 5,540,658 | 7/1996 | Evans et al. . |
| 5,593,422 | 1/1997 | Van de Moer et al. . |
| 5,630,833 | 5/1997 | Katsaros et al. . |
| 5,637,097 * | 6/1997 | Yoon .................................... 604/174 |
| 5,690,674 | 11/1997 | Diaz . |
| 5,700,277 | 12/1997 | Nash et al. . |
| 5,749,883 | 5/1998 | Halpern . |
| 5,853,399 * | 12/1998 | Sasaki .................................. 604/264 |
| 5,951,588 * | 9/1999 | Moenning ............................ 606/123 |

* cited by examiner

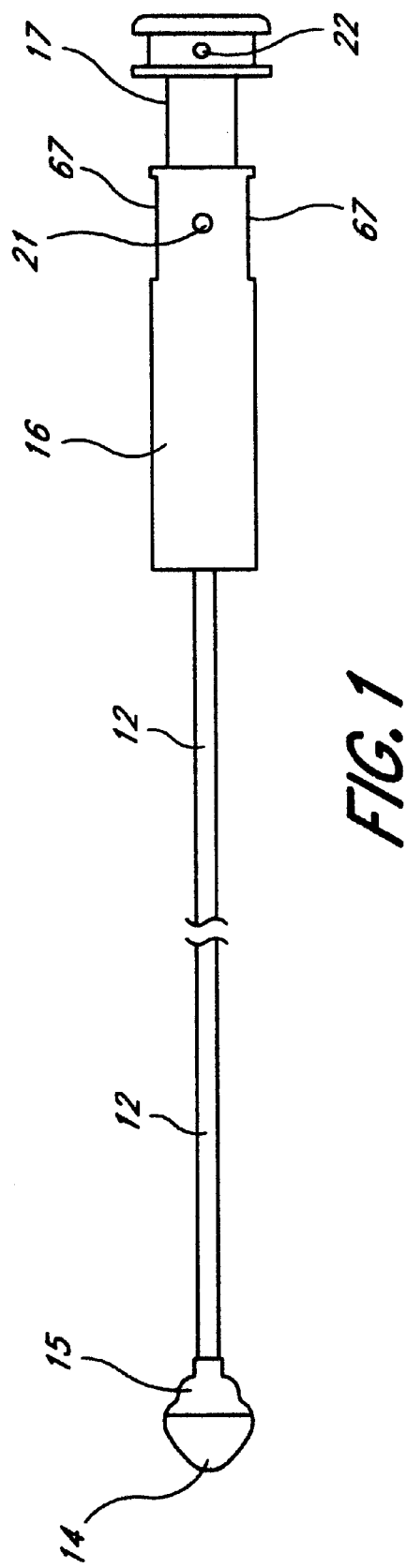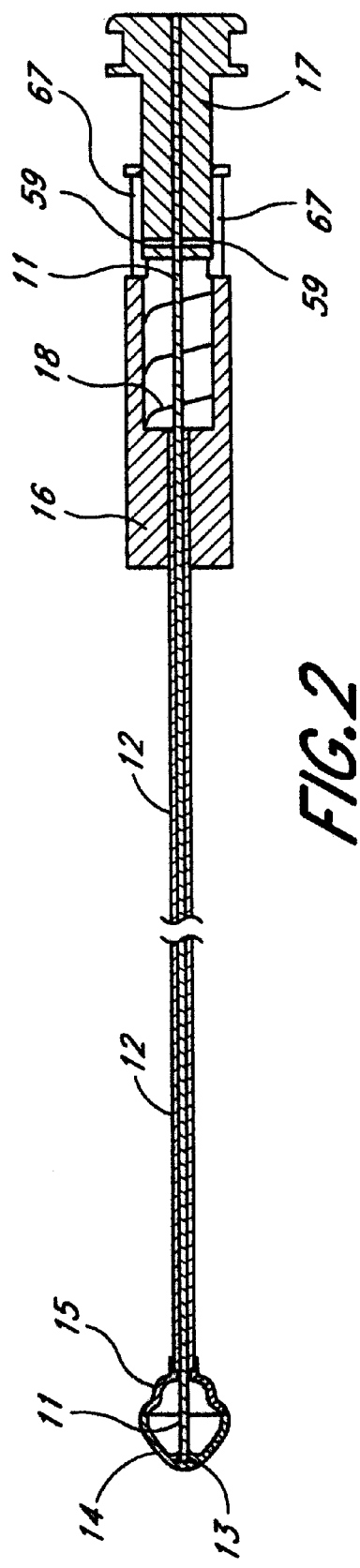

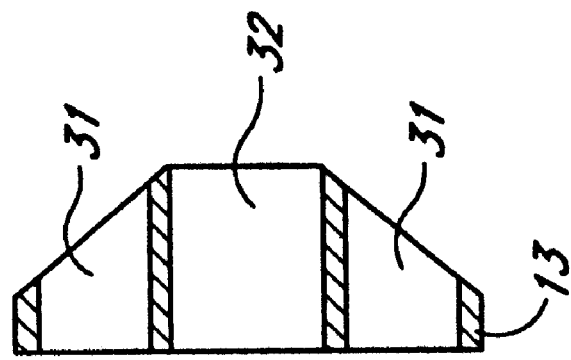
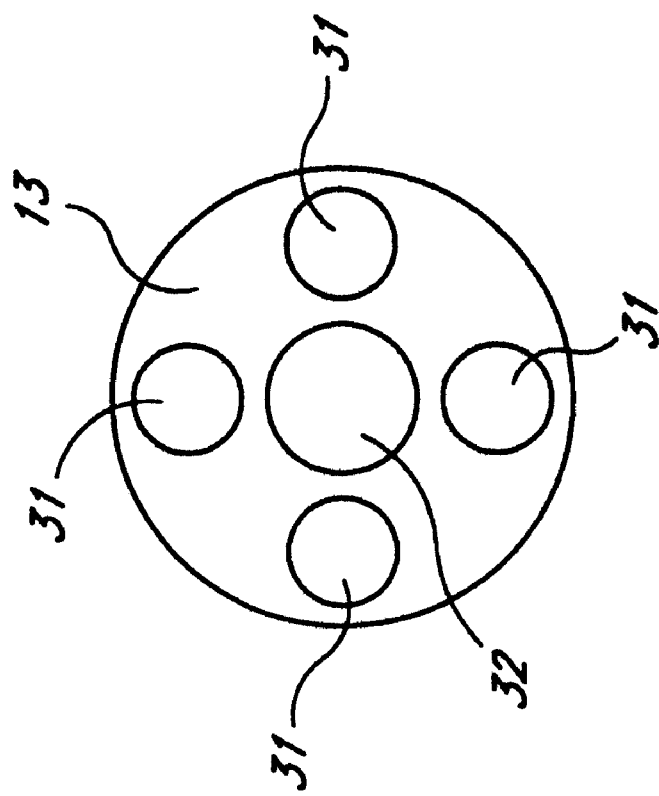

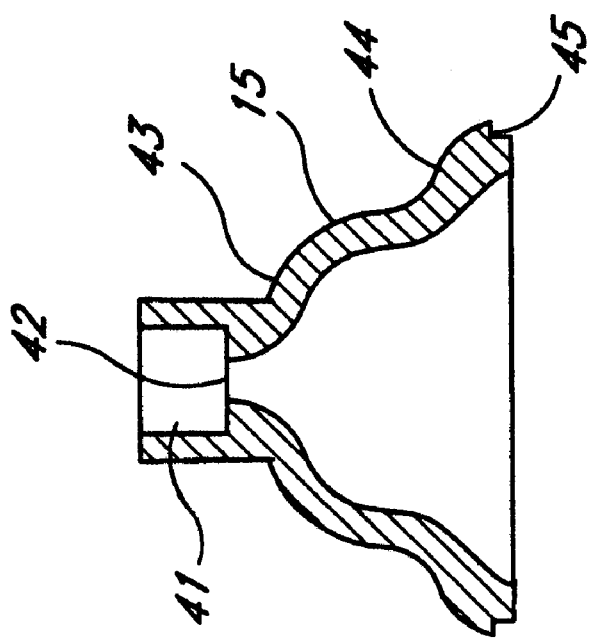
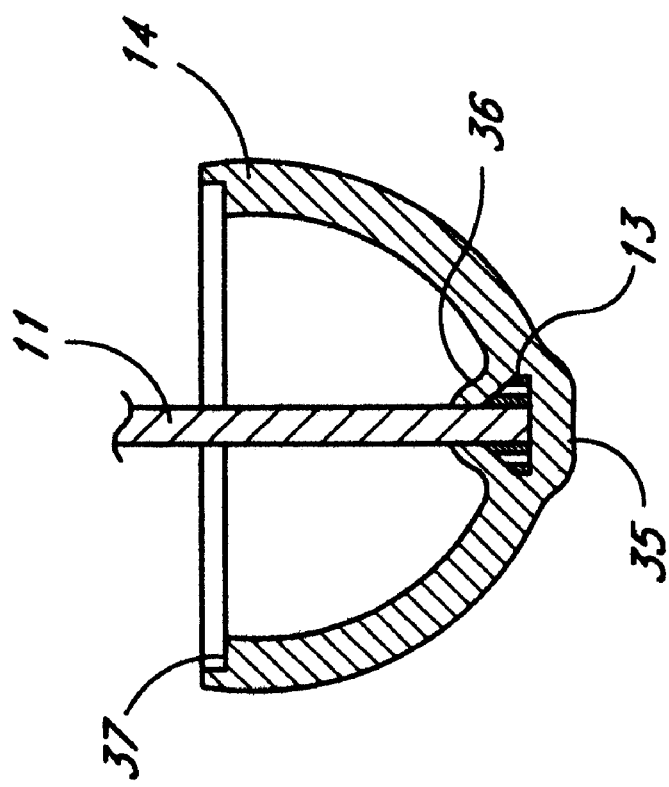
FIG. 6
FIG. 5

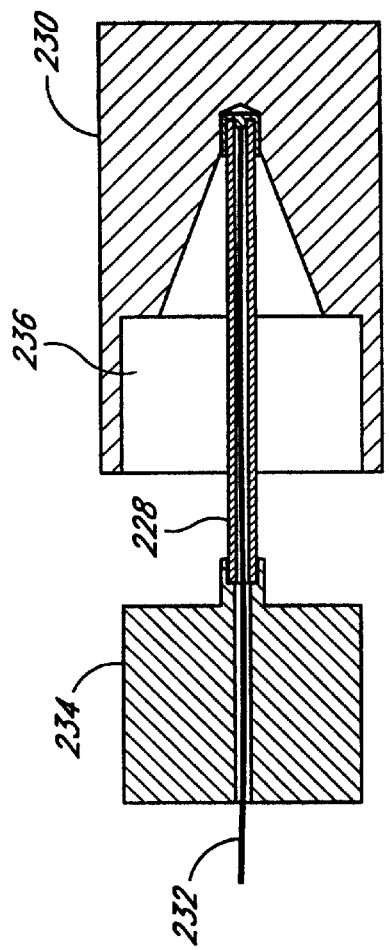
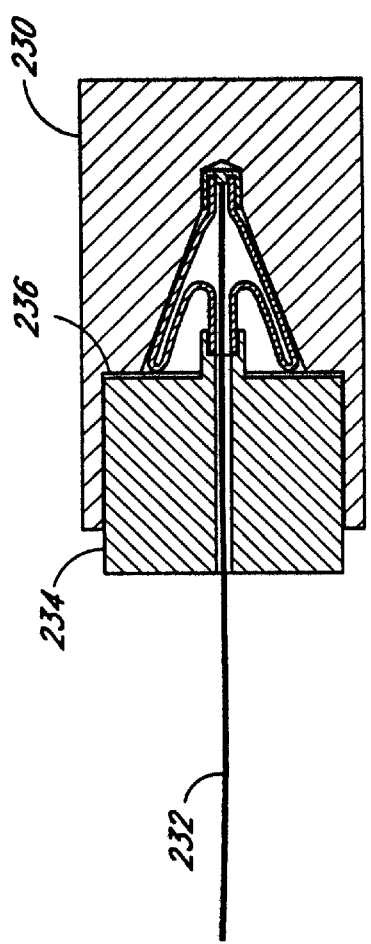
FIG.24A
FIG.24B

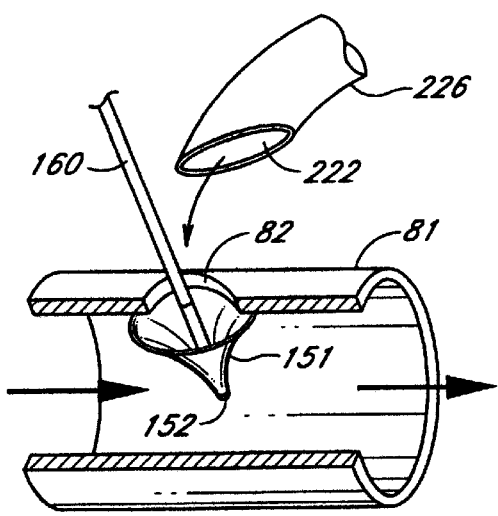
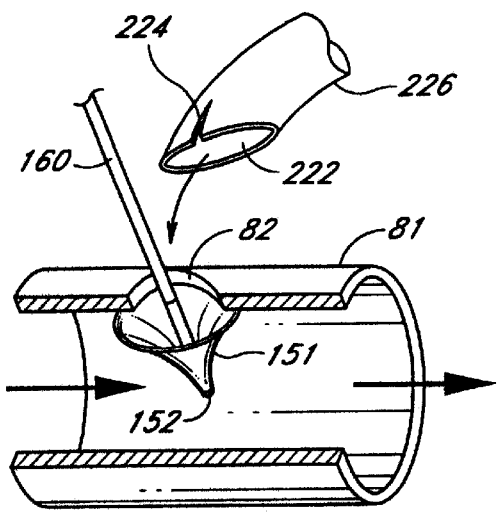
FIG.26A    FIG.26B
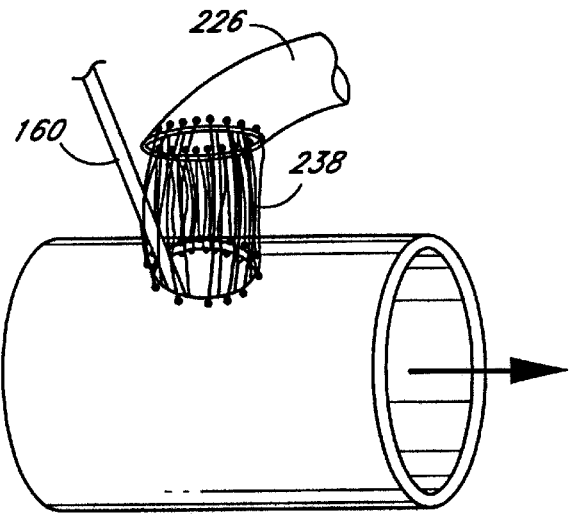
FIG.27
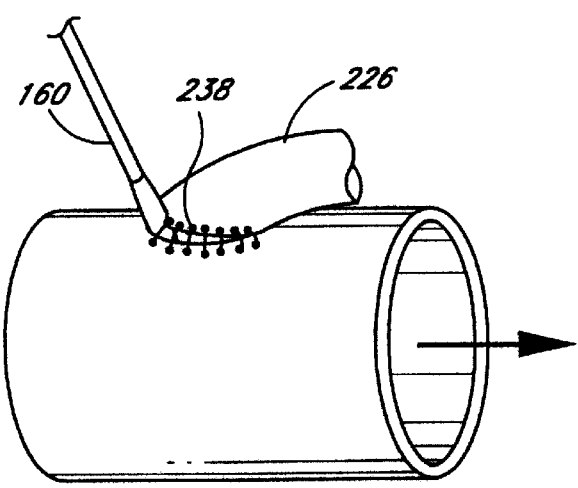
FIG.28

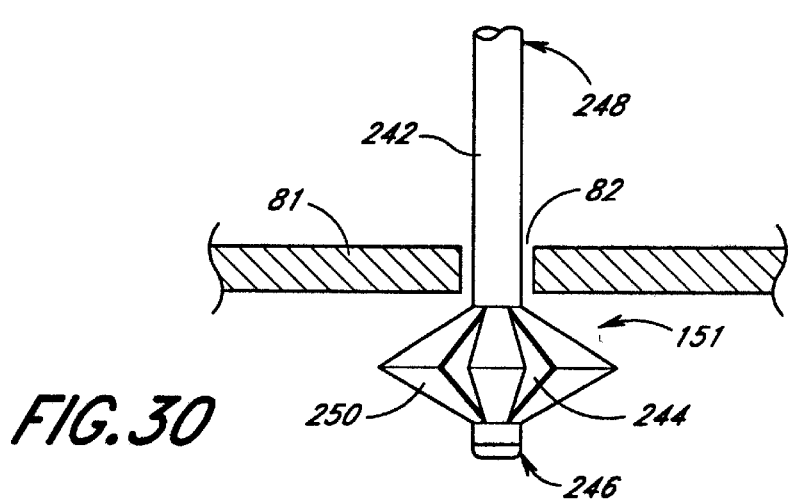
FIG.29
FIG.30
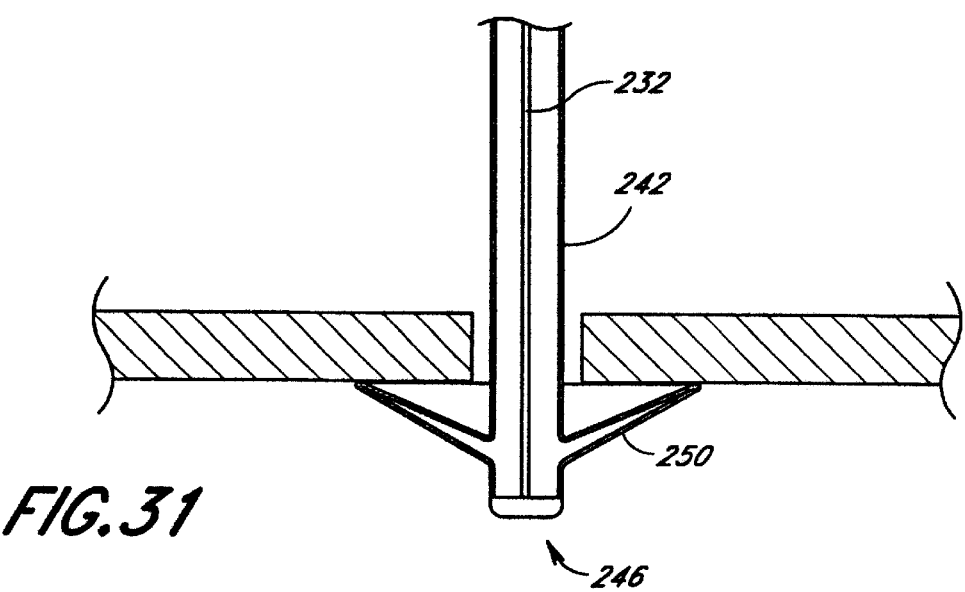
FIG.31

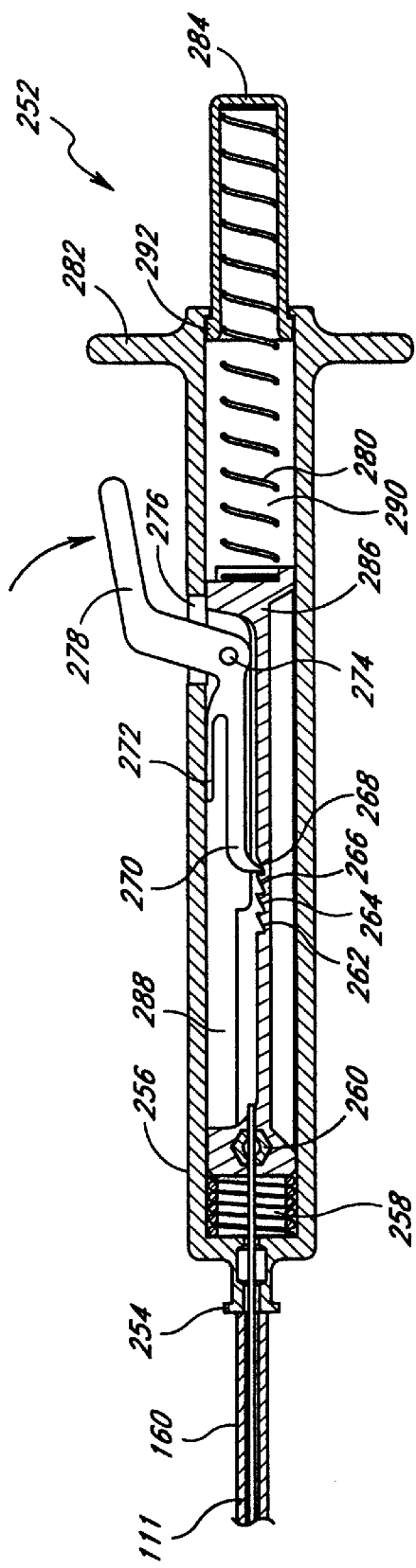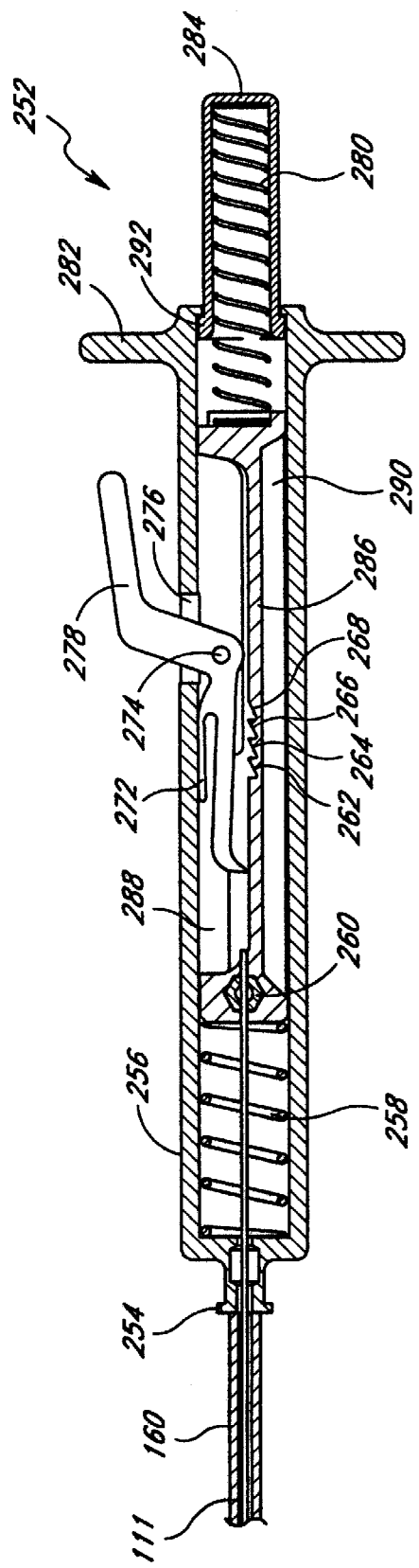

ANASTOMOSIS DEVICE WITH HOLE PUNCH

RELATED APPLICATIONS

This application claims the benefit of U.S. Provisional Application Ser. No. 60/046,972 filed May 19, 1997. This is a division of application Ser. No. 09/036,125, filed Mar. 6, 1998 now U.S. Pat. No. 5,944,730.

BACKGROUND OF THE INVENTION

1. Field of the Invention

The present invention relates generally to medical devices and methods of use thereof. Specifically, the present invention relates to medical devices used to create a seal around an incision for performing an end-to-side anastomosis procedure on the aorta or other blood vessel.

2. Description of the Related Art

Currently, the standard practice in performing a coronary artery bypass surgical procedure is to open the patient's chest, place the patient on a cardiopulmonary bypass (heart-lung) machine, stop the heart from beating, and then attach the coronary arter bypass graft(s) to the aorta and coronary arteries. The heart-lung machine is needed to maintain the blood circulation through the patient and to provide gas and heat exchange surfaces. Typically, the blood is cooled using the heart-lung machine to slow down the metabolism of the patient. Additionally, the blood is oxygenated and carbon dioxide is allowed to be released from the blood. The aorta is usually clamped proximal to the entrance point of the blood from the heart-lung machine.

There can be numerous complications with stopping the patient's heart and using a heart-lung machine. The heart-lung machine typically needs to be primed will blood. This is usually done with blood from a blood bank which can be contaminated with infectious agents such as the HIV virus. The heart-lung machine can lyse red blood cells and destroy platelets causing anemia or increasing the risk of hemorrhage. The clamping of the aorta can release plaque into the blood stream, which can cause a stroke or a peripheral vascular incident.

Another technique is to partially cross-clamp the aorta with a "U" shaped clamp such that a small blood tunnel is created and an area of blood stasis is created for making a proximal anastomosis site. This technique eliminates the heart-lung machine, but increases the risk of plaque releasing into the blood stream.

Thus, it is desirable to have a device and method that greatly reduces the risks associated with coronary artery bypass surgical procedures.

SUMMARY OF THE INVENTION

The present invention relates to a device and method for creating an anastomosis site along a wall of a blood vessel without interrupting the flow of blood through the blood vessel. The device may be used in various applications which involve incisions made in the aorta, other blood vessels or organs. The device is particularly suited to create an anastomosis site for coronary artery bypass grafts without obstructing the flow of blood in the patient's aorta. Thus, the device may be used while the patient's heart is beating without the use of a heart-lung machine or a cross clamp.

In a preferred embodiment, the device comprises an extruded hollow tube with a wire or shaft which slides within the tube. A flexible inverting member is attached to the distal end of the tube and coupled to a distal end of the shaft. A proximal portion of the shaft is coupled to an actuation assembly of the device, which preferably comprises a handle. By manipulating the handle, the practitioner can remotely deform the inverting member between two different configurations: an elongated, narrow configuration in which the inverting member may be advanced through a small incision, and an expanded, inverted configuration in which the inverting member forms a cup that can be used to form a sealed pocket against the inner wall of a blood vessel.

In operation, the medical practitioner inserts the inverting member into the blood vessel through an incision while the inverting member is in its elongated narrow configuration. The medical practitioner then manipulates the translatable shaft inside the hollow tube (preferably by manipulating a handle of the device) to expand the inverting member into its inverted configuration. The practitioner then applies a proximal force to the device to cause a seal to be formed by the radial rim of the inverting member pressing against the inner wall of the blood vessel. This prevents blood from flowing out of the incision, without obstructing the flow of blood in the blood vessel, and creates a working area for performing an end-to-side anastomosis.

In one embodiment, the device includes a hole puncher which is slidably mounted on the hollow tube. Once the seal has been formed inside the blood vessel, the hole puncher is slidably advanced distally to the outer surface of the blood vessel, and is then actuated to form an anastomosis hole around the entry point of the tube. The hole can alternatively be formed manually using a scalpel or other cutting device. In either case, the hole falls within the boundaries of the inverting member's rim, and is thus isolated from the flowing blood in the blood vessel.

Once the anastomosis hole has been formed, a bypass graft is loosely sutured around the outside of the hole while the seal is maintained between the inverting member's rim and the blood vessel's inner wall. The inverting member is then returned to the elongated, narrow configuration and withdrawn from the hole, and the ends of the suture are pulled tight to cause the end of the graft to contact the blood vessel.

These and other features and advantages of the present invention are more fully set forth in the following Detailed Description and the accompanying figures in which similar reference characters denote similar elements throughout the several views.

BRIEF DESCRIPTION OF THE DRAWINGS

FIG. 1 is a side view of one embodiment of the present invention.

FIG. 2 is a cross-sectional view of the embodiment of FIG. 1.

FIG. 3 is a top view of the retaining disk in the embodiment of FIG. 1.

FIG. 4 is a cross-sectional view of the retaining disk of FIG. 3.

FIG. 5 is a cross-sectional view of the distal inverting member in the embodiment of FIG. 1.

FIG. 6 is a cross-sectional view of an proximal inverting member in the embodiment of FIG. 1.

FIGS. 24A and 24B illustrate one method of preforming the inverting member in the embodiment of FIG. 21.

FIG. 26A illustrates how a bypass graft may be attached to the blood vessel with the inverting member inside the blood vessel.

FIG. 26B illustrates the bypass graft of FIG. 26 with a small slit to facilitate removal of the inverting member.

FIG. 27 illustrates the bypass graft of FIG. 26 being attached to the blood vessel with a purse string suture.

FIG. 28 illustrates how a practitioner pulls the ends of the purse string suture of FIG. 27 to bring the bypass graft to the blood vessel.

FIG. 29 illustrates a distal portion of a device according to a third embodiment of the present invention.

FIG. 30 illustrates how a deformable inverting member of the FIG. 29 device expands outward.

FIG. 31 is a cross-sectional view which illustrates the inverting member of the FIG. 29 device in its cup-shaped configuration.

FIGS. 32A–32B are cross-sectional views of another embodiment of the inverter control handle.

DETAILED DESCRIPTION OF THE PREFERRED EMBODIMENTS

Figure 9:
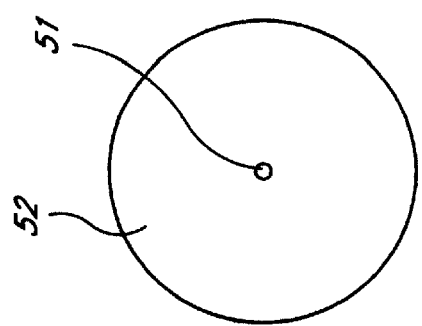
FIG. 9 is a proximal end view of the piston of FIG. 7.

Three embodiments of the invention, and several variations of these embodiments, will now be described with reference to the drawings. Other embodiments will be apparent to those skilled in the art. Although the invention is described in terms of three separate embodiments, it will be recognized that many of the features and components of these different designs can be appropriately combined and/or interchanged.

The various embodiments of the device described herein make use of a flexible, deformable member which inverts "inward" to form a cup having an opening which faces the shaft to which the flexible member is attached. The shaft is then advanced proximally (toward the physician) to draw the rim of the cup against the wall of the artery, around the entry point of the shaft. In other embodiments, a deformable member may be used which inverts or deforms "outward," so that the opening of the cup faces away from the shaft to form a plunger-like configuration. The shaft would then be pushed distally (away from the physician) to form a seal against the far wall of the artery.

First Embodiment

FIGS. 1–20 illustrate a first embodiment of the present invention. As illustrated by FIGS. 1 and 2, this embodiment comprises a proximal outer handle 16 with a translatable piston 17 slidably retained within the handle 16. Attached to the distal center of the handle 16 is a hollow extrusion 12. The extrusion 12 extends distally to the proximal inverting member 15 which is bonded to the extrusion 12 and bonded to the distal inverting member 14. The proximal and distal inverting members 15, 14 are preferably made out of a flexible compliant biocompatible material such as polyurethane, Dynaflex, silicone, and the like. The two inverting members, 14, 15 may alternatively be formed as a single member as described below.

A translatable wire 11, or other type of shaft, is attached to the center of the piston 17 and attached to the internal distal tip of the distal inverting member 14 via a retaining disk 13. The translatable wire 11 traverses through a lumen of the extrusion 12. The wire 11 and retaining disk 13 are preferably made out of a durable material such as stainless steel.

In an alternative design, the translatable wire 11 may be a thin, hollow tube, called a "hypotube," which has open ends and the distal and proximal ends of the device. This tube can be used either for bleed back or to insert a guidewire into the blood vessel.

FIG. 2 shows a spring 18 retained within the handle 16 such that it exerts force on the piston 17 to urge the piston 17 away from (and proximal to) the handle 16. This causes the wire II to be translated proximally relate to the extrusion 12 and, as explained further below, causes the inverting members 14, 15 to assume an inverted configuration.

FIGS. 3 and 4 illustrate the retaining disk 13. The retaining disk 13 is preferably cylindrical in shape with tapered sides. Provided in the center of the retaining disk 13 is a central hole 32. The translatable wire II is welded inside the central hole 32. Also provided in the retaining disk 13 are a plurality of radial holes 31 running parallel to the center hole 32. The radial holes 31 are used during the molding of the distal inverting member 14 such that the material of the distal inverting member 14 can travel through the holes 31 and a better bond can be created (see discussion below).

FIGS. 5 and 6 illustrate the distal and proximal inverting members 14, 15 respectively. The inverting members 14, 15 are preferably made out of a molded compliant biocompatible material such as polyurethane, or in the alternative, it can be made out of a braided mesh that is totally or partially covered by a compliant material. The distal inverting member 14 is preferably cup-shaped. The distal inverting member 14 is molded with the retaining disk 13 and wire 11 in place, allowing the material to be formed within the radial holes 31 of the retaining disk 13. The distal member 14 is thickest at the distal tip 35 and has an additional inner cone 36 that is formed around the proximal surface of the retaining disk 13. The proximal end of the distal inverting member 14 has a notch 37 for mating with the proximal inverting member 15.

The proximal inverting member 15 is also cup shaped. The sides of the cup are somewhat serpentine shaped and have two concave portions 43 and 44 respectively when viewed from the outside. The distal end of the proximal inverting member 15 has a notch 45 for mating with the notch 37 of the distal inverting member 14. At the proximal apex there is provided a cylindrical tunnel 41 for bonding to the outer surface of the extrusion 12. A central smaller hole 42 is provided for the translatable wire 11 to travel through.

Figure 7:
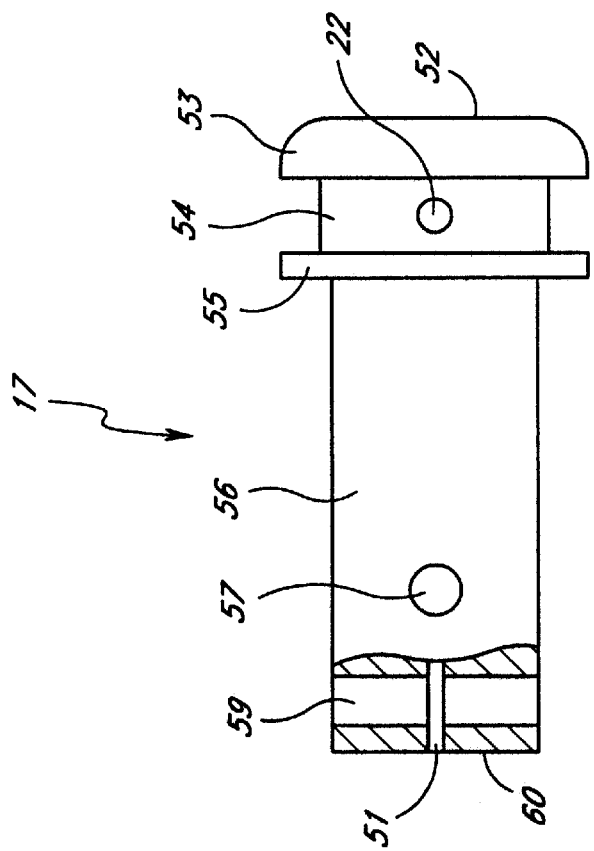
FIG. 7 is a side view, partially in cross-section, of a piston in the embodiment of FIG. 1.
Figure 8:
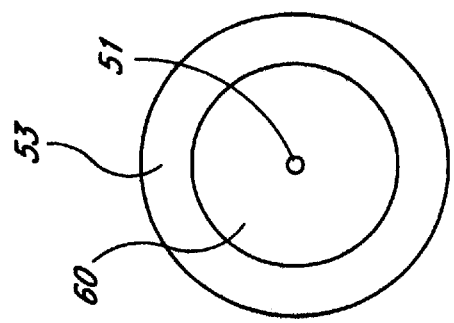
FIG. 8 is a distal end view of the piston of FIG. 7.
Figure 10:
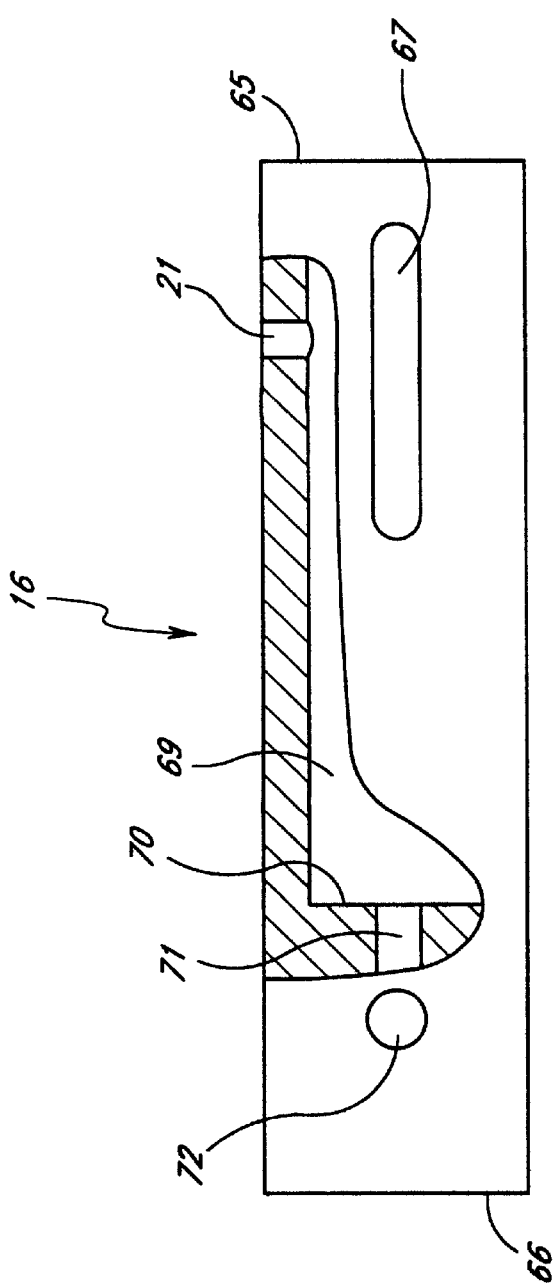
FIG. 10 is a side view, partially in cross-section of the handle in the embodiment of FIG. 1.

FIGS. 7–9 illustrate the translatable piston 17. The piston is essential cylindrical in shape with a proximal flat surface 52 and a distal flat surface 60. Provided within the center of the piston 17 is a shaft 51 for mounting the translatable wire 11. A set screw hole 22 is provided along the side of the piston 17 for placing a set screw (not shown) to purchase the translatable wire 11. Holes 59 are also provided along the sides 56 of the piston to allow for the placement of retaining pins. The retaining pins travel in the retaining slots 67 of the handle 16 (FIG. 10). A third hole 57 is provided for pinning the piston 17 in a neutral position for storing the device when not in use. The most proximal end of the piston 17 has a thumb rest 53.

Figure 12:
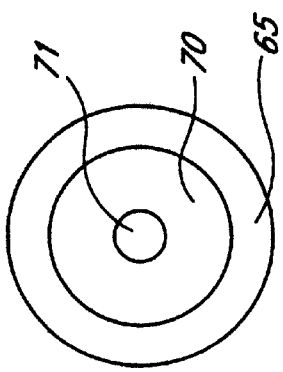
FIG. 12 is a proximal end view of the handle of FIG. 10.
Figure 11:
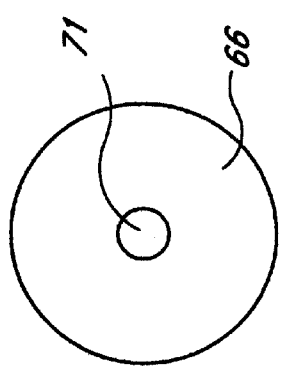
FIG. 11 is a distal end view of the handle of FIG. 10.

FIGS. 10–12 illustrate the handle 16 in further detail. The handle 16 is a cylindrical member that is partially hollowed out to receive the piston 17. The piston 17 travels in the bore 69 which ends at floor 70. The spring 18 is placed in the bore 69 between the floor 70 and the distal end 60 of the piston 17. The extrusion 12 in FIGS. 1 and 2 is inserted into a lumen 71 in the distal end 66 of the handle 16 and is set in place by a set screw threaded through hole 72. A pinning hole 21 is provided near the proximal end 65 to pin the piston 17 in a neutral position. Slots 67 are provided on opposite sides of the handle 16 to limit the travel of the piston 17.

Figure 13:
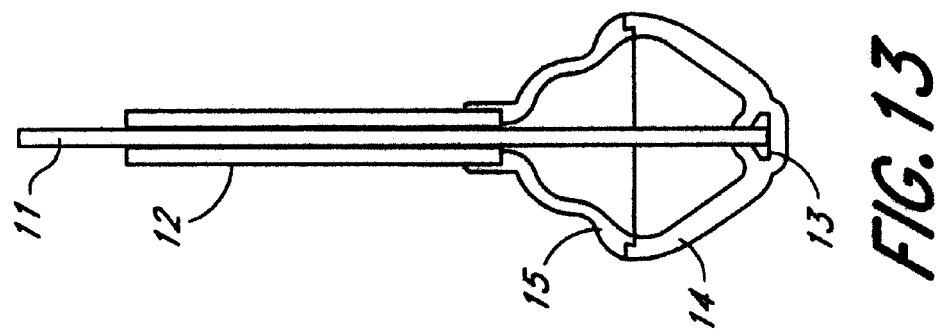
FIG. 13 is a schematic cross-sectional view of the inverting member in the embodiment of FIG. 1 in its resting configuration.

FIGS. 13–16 illustrate the distal end of the device of FIG. 1 in operation. When the device is stored or shipped, the piston 17 is pinned in a neutral position as illustrated in FIG. 13. In the description below, the device is used to create a working area for coronary artery bypass grafts to the aorta. The device may, however, conceivably be used in a variety of other operations involving incisions in blood vessels or organs.

Figure 15:
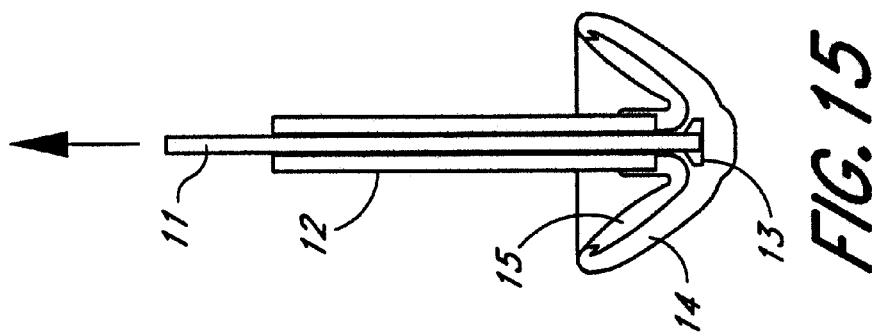
FIG. 15 is a schematic view of the inverting member of FIG. 13 in its inverted, cup-shaped configuration.
Figure 14:
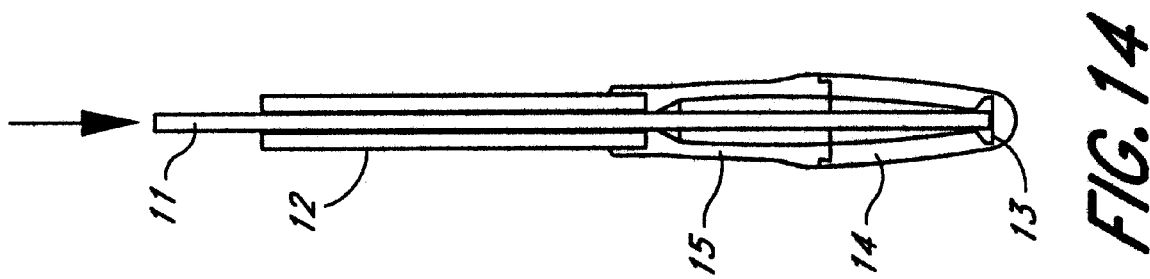
FIG. 14 is a schematic cross-sectional view of the inverting member of FIG. 13 in its stretched, elongated and narrow configuration.

In coronary artery bypass grafting, the patient is prepped and access to the aorta is established by either an open chest procedure, port access, or via a small lateral incision in the ribs. Once the aorta is accessed, a small incision 82 (FIG. 25A) is made in the aorta at a proximal anastomosis site for a coronary artery bypass procedure. The inverting members 14, 15 are then extended by translating the wire 11 distally using the piston 17 as illustrated in FIG. 14. This changes the configuration of the inverting members 14, 15 to an elongated, narrow configuration. The inverting members 14, 15 are then placed within the aorta through the small incision 82. The inverting members, 14, 15 are then "inverted" by quickly translating the wire 11 proximally as illustrated in FIG. 15. This is achieved by releasing all force on the piston 17 to let the spring 18 in the handle 16 move the wire 11 proximally. The inverting members 14, 15 change to an inverted position, forming a cup-shaped space within the inverting members 14, 15.

Figure 16:
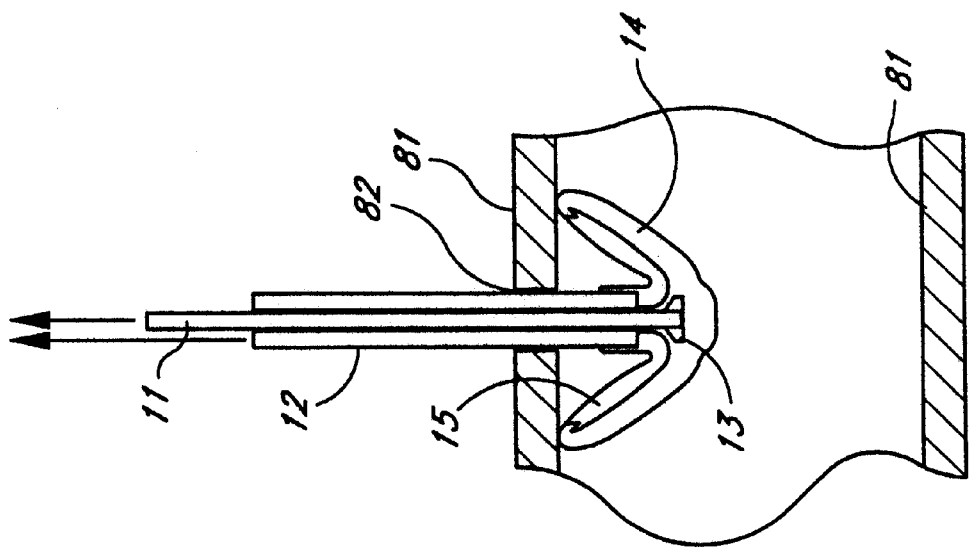
FIG. 16 is a schematic view of the inverting member of FIG. 13 in its inverted, cup-shaped configuration inserted in a blood vessel to partially occlude the vessel and completely occlude a surgically created incision in the vessel.

Next, the operator applies proximally directed tension to the device to seal the edges of the cup to the inner wall 81 of the aorta as illustrated in FIG. 16. The device only occludes the area of the aorta around the incision 82 and does not otherwise obstruct the flow of blood in the aorta. Blood flows from the heart, past the distal end of the distal inverting member 14, and to the peripheral tissues. Thus, the device prevents blood from escaping the surgical site but does not require the heart to be stopped. Once the seal has been formed to provide a working area, the medical practitioner widens the incision as needed to create a proximal anastomosis site for a coronary bypass graft. The practitioner then loosely sutures one end of a coronary artery bypass graft (typically a section of a saphenous vein) to the hole. The practitioner allows enough slack on the suture to be able to remove the device. The procedure for attaching the graft is described further below in connection with a second embodiment of the invention.

After the suture or sutures are in place, the practitioner translates the wire 11 distally to cause the inverting members 14, 15 to reform the elongated and narrow configuration as illustrated in FIG. 14. The practitioner then removes the inverting member from the aorta around the loose sutures and pulls the sutures around the graft tight to give the graft a good seal. The other end of the coronary artery bypass graft is attached to a surgically created hole in a coronary artery while the heart is still beating before, during, or after the aortic anastomosis. The rest of the coronary bypass procedure is completed using standard techniques.

FIGS. 17–20 illustrate various designs of an alternative inverting member 151. The inverting member 151 is preferably a single piece and is created out of a braided tube 115, such as one-quarter inch expandable sleeving, which is often used to house electrical conduits. The braids can be made out of nylon, plastic, or the like. The inverting member 151 is preferably in the form of a wireloom weave. The distal end 116 of the braided tube 115 is glued to a wire 111. The proximal end 117 of the tube 115 is glued via adhesive to the distal end of the extrusion 112.

Figure 17:
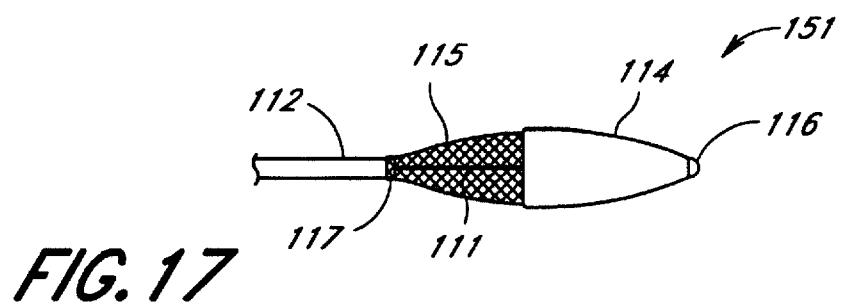
FIGS. 17 and 17A are side views of another design of the inverting member extended in an elongated, narrow configuration.
Figure 17A:
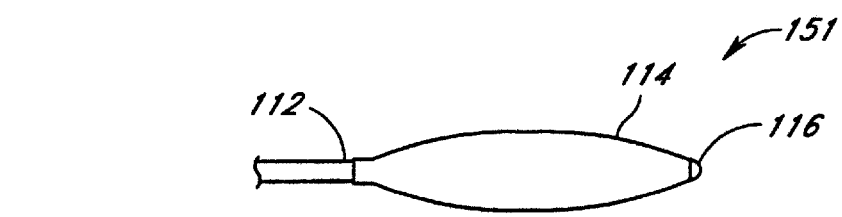
Figure 18:
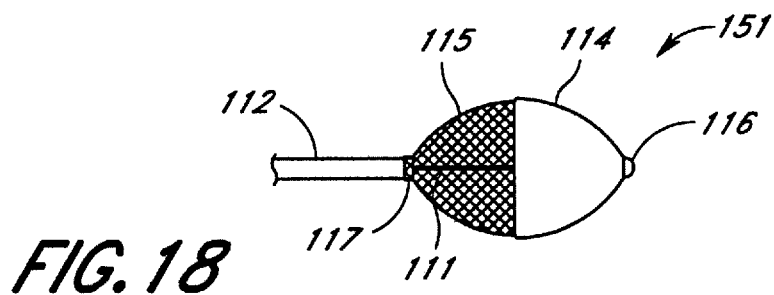
FIG. 18 is a side view of the inverting member of FIG. 17 in a neutral configuration.
Figure 19:
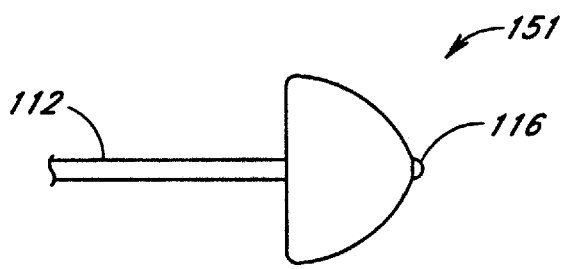
FIG. 19 is a side view of the inverting member of FIG. 17 in an inverted configuration.
Figure 20:
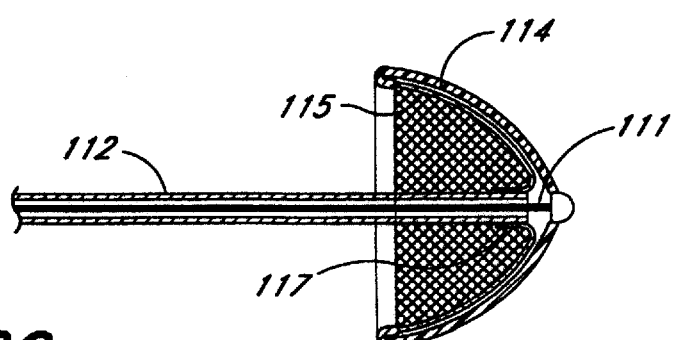
FIG. 20 is a cross-sectional view of the inverting member of FIG. 19.

In the preferred embodiment, the entire inverting member 151 preferably is covered with a flexible material such as silicone. This is shown in FIG. 17A. This flexible material is preferably impermeable so that blood cannot seep through the expandable sleeving 115. Three coats of silicone are preferably applied to the expandable sleeving 115. Alternatively, only the distal half 114 or two-thirds of the tube 115 is coated with the silicone coats. This is shown in FIGS. 17, 18, and 19.

A handle and piston are attached to the proximal end of the extrusion 112. The handle and piston can be the same as described above and are not illustrated.

This inverting member 151 generally operates in the same manner as the inverting members 14, 15 described above. When the operator translates the wire 111 distally, the inverting member 151 assumes an elongated and narrow configuration as illustrated in FIG. 17. When the operator causes the wire 111 to move proximally relative to the extrusion 112, the inverting member 151 expands radially and then inverts, as illustrated in FIGS. 18 and 19.

Second Embodiment

Figure 21:
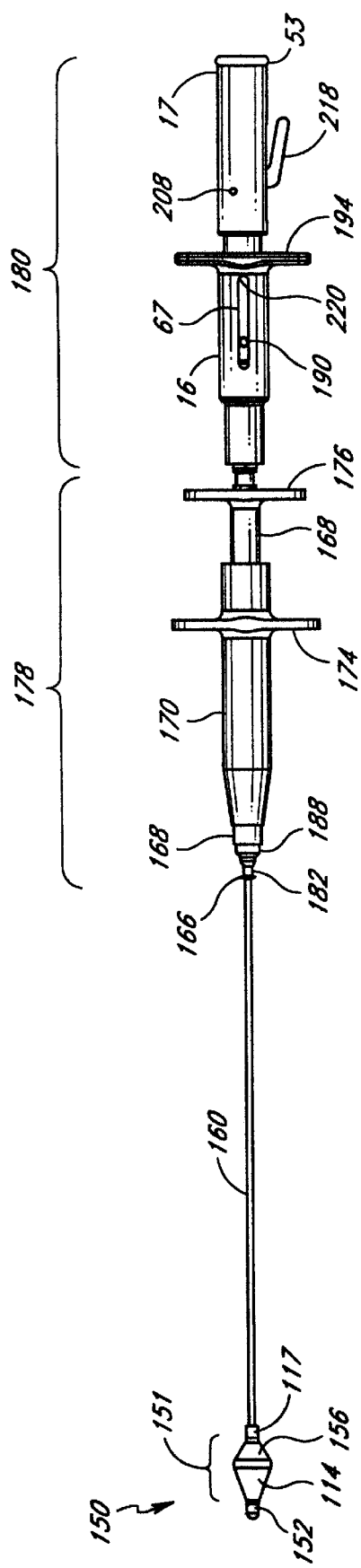
FIG. 21 is a side view of another embodiment of the present invention.

A device according to a second embodiment of the invention will now be described with reference to FIGS. 21–26, 32A and 32B. As illustrated in FIG. 21, the device features a flexible one-piece inverting member with a handle 180 and hole puncher 178. In a preferred embodiment, the inverting member 151 in FIG. 21 is similar to the one-piece inverting member 151 described above and illustrated in FIGS. 17–20.

FIGS. 24A–24B illustrate a manufacturing process for preforming the inverting member 151 to cause it to assume the configurations generally shown in FIGS. 17–20 upon the application of an appropriate biasing force. This process is preferably performed before the inverting member 151 is attached to the other parts of the device.

In FIG. 24A, a rod 232 is inserted through the expandable sleeving 228. As shown in FIG. 24A, both the rod 232 and the expandable sleeving 228 are inserted into a compression mold 230. A compressor 234 at the proximal end is slidably received in the compression mold 230. Both the compressor 234 and the compression mold 230 are preferably cylindrical and made of stainless steel. The compressor 234 pushes (inverts) the proximal end of the expandable sleeving 228 into the rest of the sleeving 228 until the compressor 234 reaches its compressor groove 236. The sleeving 228 is held in this position and pressure is applied to form a crease in the sleeving 228. The sleeving 228 will thereafter naturally deform into this configuration if pressure is applied to the proximal inverting portion 156. This preforming method may be done solely with pressure and without heat.

Figure 22A:
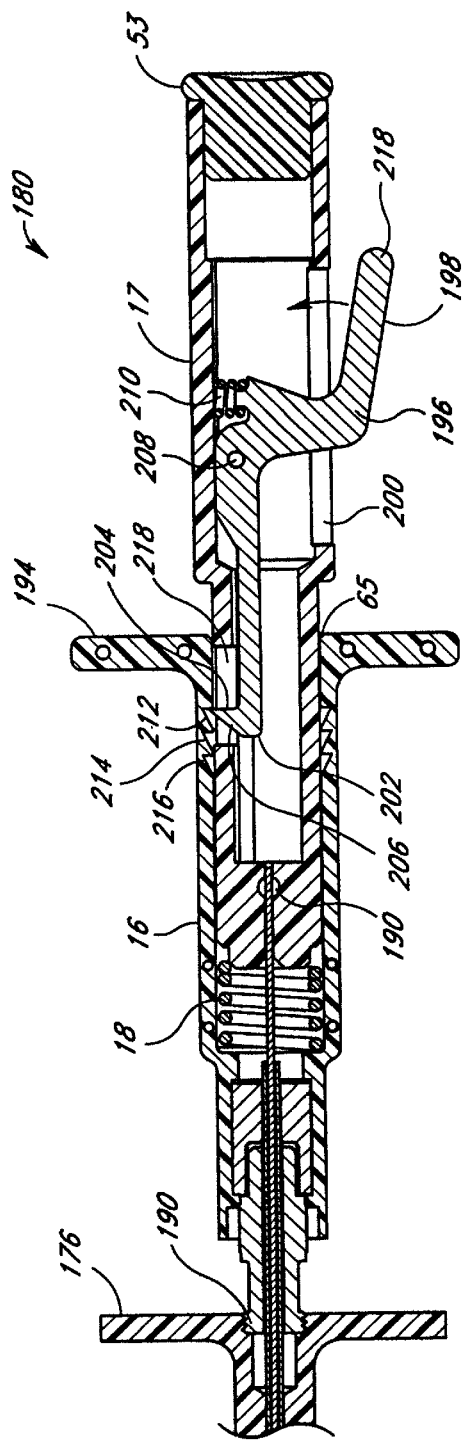
FIG. 22A is a cross-sectional view of the inverter control handle in the embodiment of FIG. 21.

FIG. 22A is a cross-sectional view of the inverter control handle 180 of the embodiment illustrated in FIG. 21. The inverter control handle 180 comprises a translatable, hollow piston 17 and a proximal outer handle 16. As in the embodiments described above, the translatable piston 17 of the inverter control handle 180 may be cylindrical in shape and slidably retained inside outer handle bore 69. The operation of the inverter control handle 180 in this embodiment is generally the same as in the embodiment described above, except for the differences noted below.

The piston spring 18 within the outer handle bore 69 exerts force on the translatable piston 17 in a proximal direction, away from the outer handle 16. A retaining pin 190 on the piston 17 protrudes radially from piston 17 and slides in a retaining slot 67 (in FIG. 21) on the outer handle 16. When the retaining pin 190 is at the proximal end 220 of the retaining slot 67. the stabilizing force of the retaining pin 190 counters the force of the piston spring 18 and keeps the piston 17 from sliding out of the outer handle 16. The control handle 180 has a pair of retaining pins 190 and slots 67, located on opposite sides of the piston 17 and outer handle 16. When the piston 17 is extended to its farthest distance from the outer handle 16 as in FIG. 22B, the inverting member 151 is in its inverted configuration.

Figure 22B:
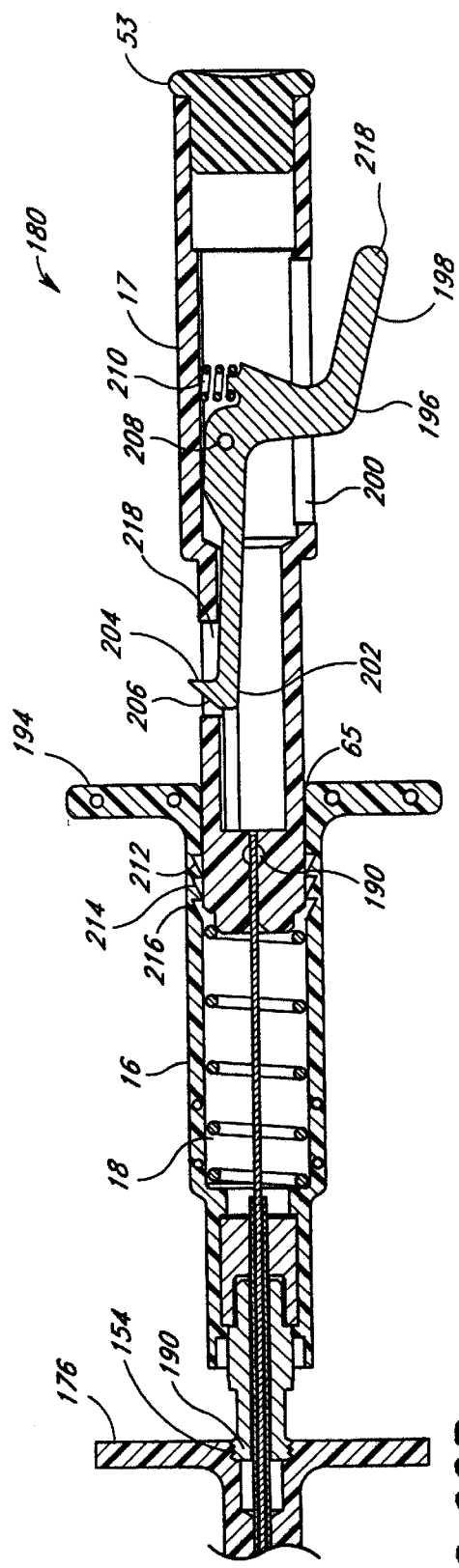
FIG. 22B is a cross-sectional view of the translatable, hollow piston of FIG. 21 in its most proximal position.

A releasor 196 pivots on a releasor pin 208, which is attached to the interior of the hollow piston 17. A releasor spring 210 exerts force on the releasor 196 and keeps the releasor lever 218 in its extended position, the position farthest from the piston 17. This is shown in FIG. 22A. The lever 218 of the releasor 196 protrudes from the exterior surface of the piston 17 through a releasor aperture 200. A releasor 25 latch 202, located at the distal end of the releasor 196, protrudes from the exterior surface of the piston 17 through a latch aperture 218. This is shown in FIG. 22B.

Figure 22C:
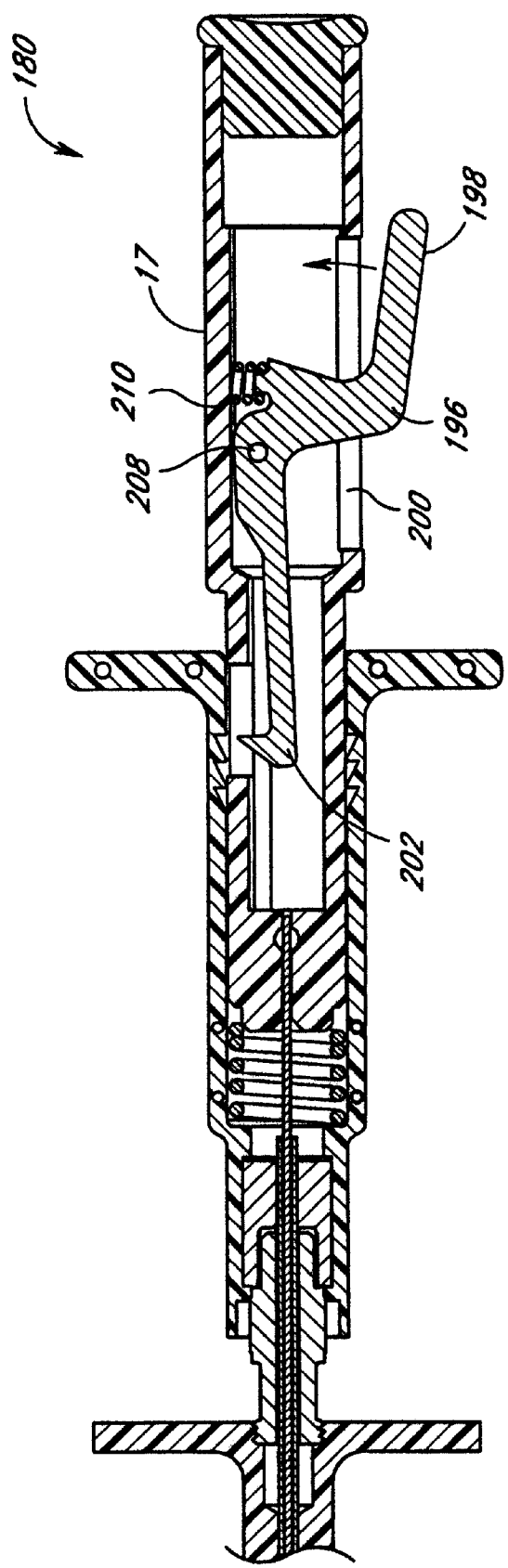
FIG. 22C is a cross-sectional view of the translatable, hollow piston and releasor of FIG. 21.

By pushing the releasor lever 218 toward the piston 17, the releasor spring 210 compresses, and the releasor 196 pivots on the releasor pin 208. This is shown in FIG. 22C.

There are preferably three position grooves 212, 214, 216 molded into the internal surface of the handle bore 69. These grooves 212, 214, 216 are used to catch and hold the releasor latch 202. More than three grooves may alternative be included to provide for more than three positions of the inverting member 151.

The use and operation of the inverter control handle 180 will now be described with reference to FIGS. 21–23. First, the medical practitioner braces his or her fingers on finger grips 194 on the outer handle 16 and pushes the thumb (or palm) rest 53 distally toward the handle 16 to stretch the inverting member 151 into its elongated, narrow configuration. This pushes the piston 17 into the handle bore 69 and compresses the piston spring 18 within the handle bore 69. Continued pressure on thumb rest 53 causes the angled surface 206 of the releasor latch 202 to come in contact with the proximal end 65 of the handle 16. The angled surface 206 allows the releasor latch 202 to slide smoothly into the handle bore 69. This causes the releasor spring 210 to compress.

The releasor latch 202 continues to slide inside the handle bore 69 until the releasor latch 202 falls into a first position groove 212. This is shown in FIG. 22A.

When the latching surface 204 of the releasor slides into the first position groove 212, the combined forces of the piston spring 18 and the releasor spring 210 lock the piston 17 into a first position. In this first position, the inverting member 151 is about two-thirds extended to its elongated, narrow configuration. This configuration may or may not be narrow enough to insert or withdraw the inverting member 151 into or out of the incision made in the blood vessel.

If this retracted configuration is not narrow enough, the medical practitioner pushes on thumb rest 53 until the releasor latch 202 slides into a second position groove 214. In this second position, according to one embodiment, the inverting member is about four-fifths extended to its elongated, narrow configuration. If this configuration is still not narrow enough, the medical practitioner pushes on thumb rest 53 until the releasor latch 202 slides into a third position groove 216. In this third position, the inverting member is roughly nine-tenths or all the way extended to its elongated, narrow configuration. The practitioner can then insert or withdraw the inverting member 151 into or out of an incision made in a blood vessel.

In an alternative design, the distal tip 152 of the inverting member 151 may be used to create the initial incision. In this case, the inverting member 151 slide in through the incision immediately after the incision is made.

When the releasor latch 202 is in any of the position grooves 212–216, the practitioner can transform the inverting member 151 into its inverted configuration instantly by pressing the releasor lever 218. Specifically, the practitioner pushes the releasor activation surface 198 toward the piston 17. The releasor spring 210 compresses and the releasor latch 202 lifts out of its current position groove. This releases the piston 17 from its locked position, and the piston spring 18 instantly snaps the piston 17 back to its most proximal position. The retaining pin(s) 190, comes in contact with the proximal end of the retaining slot 67 to prevent the piston 17 from shooting out of the handle bore 69.

This sudden snapping motion inverts the inverting member 151 to its inverted configuration instantly so that a minimum amount of blood escapes through the incision 82 in the blood vessel. The quicker the inverting member 151 inverts, the quicker a seal can be formed against the inner walls of the blood vessel. Next, proximally directed tension is applied to the device to seal the edges of the inverting member to the wall of the blood vessel.

FIGS. 32A and 32B illustrate an alternative handle implementation for the FIG. 21 device. The inverter control handle 252 comprises a hollow outer handle 256, a first piston spring 258, a second piston spring 280, a translatable piston 286, a releasor 270, and a translatable compressor 284. The operation of the inverter control handle 252 shown in FIGS. 32A-32B is generally the same as in the embodiments described above, except for the differences noted below.

The distal end 254 of the outer handle 256 is attached to the proximal end of the flexible extrusion (tube) 160. The distal portion 260 of the piston 286 is attached to the proximal end of the translatable wire 111. The first piston spring 258 within the out handle bore 290 exerts force on the translatable piston 286 in a proximal direction The second piston spring 280 within the outer handle bore 290 exerts a force on the translatable piston 286 in a distal direction, which counters the force of the first piston spring 258 and keeps the piston 286 from sliding out of the outer handle 256. The second piston spring 280 also exerts a force on the translatable compressor 284 in a proximal direction. The distal end 292 of the compressor 284 is formed so that it prevents the compressor from sliding completely out of the outer handle bore 290. The piston 286 is also formed with a groove 288 to slidably receive the releasor 270. When the piston 286 is extended to its farthest proximal position as in FIG. 32B, the inverting member 151 is in its inverted configuration.

The releasor 270 pivots on a releasor pin 274, which is attached to the interior of the hollow handle 256. A flexible releasor support pin 272 exerts force on the releasor 270 and keeps the distal end of the releasor 270 in contact with the piston 286. The support pin 272 performs basically the same function as the releasor spring 210 in FIG. 22A described above. The lever 278 of the releasor 270 protrudes from the exterior surface of the handle 256 through a releasor aperture 276. By pushing the releasor lever 278 toward the handle 256, the releasor support pin 272 compresses, and the releasor 270 pivots on the releasor pin 274. This is shown in FIG. 32B. There are preferably four position grooves 262, 264, 266, 268 molded into the internal surface of the piston 286. These grooves 262, 264, 266, 268 are used to catch and hold the piston 286. More than four grooves may alternatively be included to provide for more than four positions of the inverting member 151.

The use and operation of the inverter control handle 252 will now be described with further reference to FIGS. 32A–32B. First, the medical practitioner begins with the inverter control handle 252 in the position shown in FIG. 32B. The practitioner braces his or her fingers on finger grips 282 on the outer handle 256 and pushes the translatable compressor 284 distally to stretch the inverting member 151 into its elongated, narrow configuration. This pushes the second piston spring 280 distally within the handle bore 290 into the piston 286 and compresses the first piston spring 258. Continued pressure on compressor 284 causes the distal end of the releasor 270 to slide inside the piston groove until the distal end of the releasor 270 falls into a first position groove 262.

When the distal end of the releasor 270 slides into the first position groove 262, the combined forces of the first piston spring 258, the second piston spring 280 and the releasor support pin 272 lock the piston 286 into a first position. In this first position, the inverting member 151 is partially extended to its elongated, narrow configuration. With the handle 252 in this position, the inverting member 151 may or may not be narrow enough to inserted or withdrawn through the incision 82 (FIG. 5A) made in the blood vessel.

If the inverting member is not stretched to a sufficiently narrow configuration at this stage, the medical practitioner can further reduce the cross sectional circumference of the inverting member 151 by pushing the compressor 284 until the distal end of the releasor 270 slides into a second, third or fourth position groove 264, 268, 268. Once the desired configuration has been obtained, the practitioner inserts or withdraws the inverting member 151 into or out of the incision.

When the distal end of the releasor 270 is in one of the position grooves 262–268, the practitioner can transform the inverting member 151 into its inverted configuration instantly by pressing the releasor lever 278 in the direction of the arrow in FIG. 32A. Pressing the releasor lever 278 causes the releasor support pin 272 to bend inward, and causes the distal end of the releasor 270 to lift out of the current position groove. This releases the piston 286 from its locked position, and the first piston spring 258 instantly snaps the piston 286 back to its most proximal position. The second piston spring 280 prevents the piston 286 from shooting out of the handle bore 290.

This sudden snapping motion inverts the inverting member 151 to its inverted configuration instantly so that a minimum amount of blood escapes through the incision 82 in the blood vessel. Next, upward or proximal tension is applied to the device (preferably from the handle) to seal the edges of the inverting member to the inner wall of the blood vessel.

Figure 23:
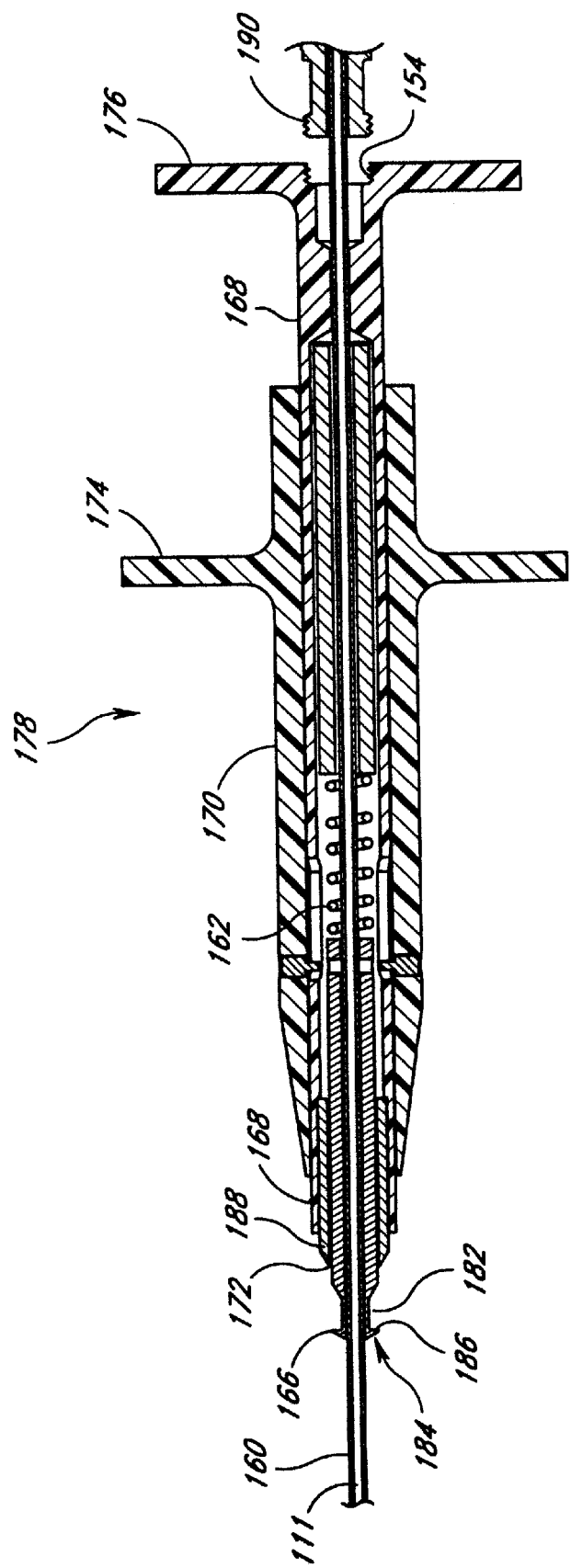
FIG. 23 is a cross-sectional view of the hole puncher of FIG. 21.

FIG. 23 is a cross-sectional view of the hole puncher 178 of FIG. 21. In one application of the present invention, the hole puncher 178 may be used to widen the initial slit incision 82 made in the aorta to create a proximal anastomosis site for a coronary bypass graft. The widened hole is preferably circular in shape, but may be elliptical.

The entire hole puncher 178 is preferably slidable along the extrusion 160 between the inverting member 151 and the inverter control handle 180. The proximal end of the hole puncher 178 preferably has a cylindrically-shaped bore 154, which is internally threaded to receive the threaded distal end 190 of the inverter control handle 180. The hole puncher 178 is screwed onto the distal end 190 of the inverter control handle 180 to prevent the hole puncher 178 from obstructing the practitioner's way and interfering with the suturing and grafting process. This is shown in FIG. 23. Alternatively, instead of a screw-type attachment, the attachment may be a clip or lock configuration. The connecting screw or lock may be designed in a variety of ways.

The hole punch outer handle 170 is attached to the hole punch shaft 182. This attachment may be accomplished by a pin or other connecting piece. The hole punch inner handle 168 is slidably retained inside the outer handle 170 and is attached to the hole punch enforcer 188. Hole punch spring 162 resides inside the hollow inner handle 168 and exerts pressure to keep the inner handle 168 in an extended proximal position. Thus, when the hole puncher is dormant, the inner handle finger grips 176 and the outer handle finger grips 174 are at their maximum distance apart from one another.

When the medical practitioner pushes the inner handle finger grips 176 toward the outer handle finger grips 174 (against the force of the spring 162), the hole punch enforcer 188 slides out further from the outer handle 170 (this motion may also be described as pulling the outer handle finger grips 174 towards the inner handle finger grips 176). Also, the hole punch shaft 182 slides further into the hole punch aperture 172 because the hold punch shaft 182 is attached to the outer handle 170. The hole punch enforcer 188 continues to slide until it meets the radial edge 184 of the hole punch head 166. If the practitioner continues to push, the hole punch head 166 slides inside the hole punch aperture 172, leaving the hole punch enforcer 188 as the most distal piece of the hole puncher 178.

Figure 25C:
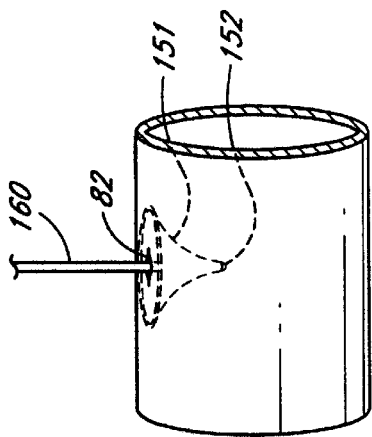
FIG. 25C illustrates the inverting member of FIG. 25B expanding in the blood vessel to create a seal.
Figure 25B:
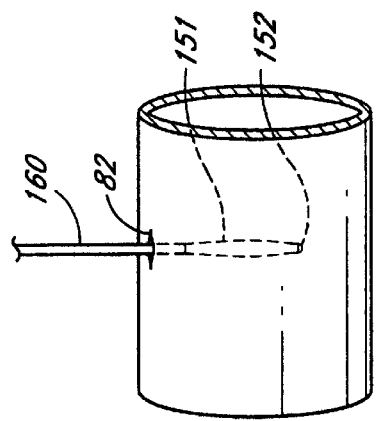
FIG. 25B illustrates the inverting member inserted into the incision of FIG. 25A.
Figure 25A:
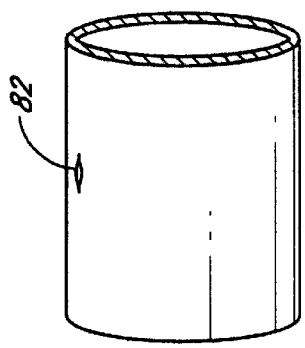
FIG. 25A illustrates how an incision is made in the side of a blood vessel.
Figure 25E:
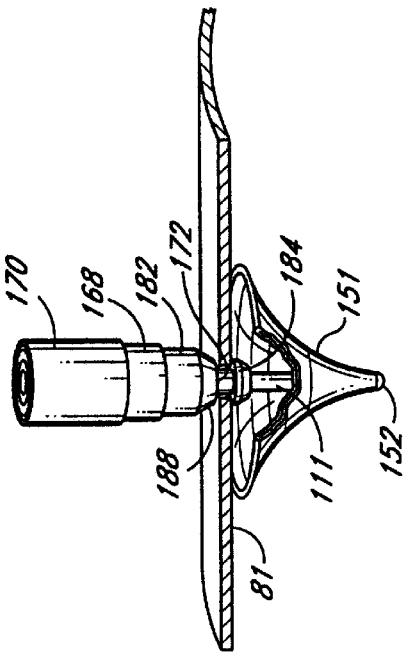
FIG. 25E illustrates the operation of the hole puncher of FIG. 25D.
Figure 25D:
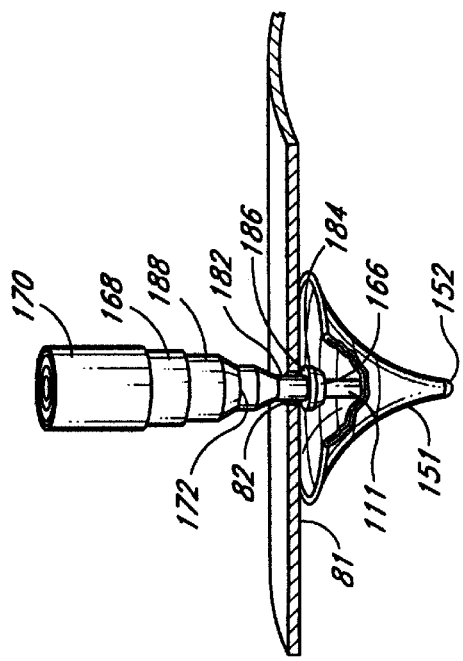
FIG. 25D illustrates the insertion of the hole puncher of FIG. 21.

The use and operation of the hole puncher 178 will now be described with reference to FIGS. 25A–25E and 26. As described above, the medical practitioner makes an initial slit incision 82 in the blood vessel as shown in FIG. 25A. The practitioner inserts the inverting member 151 in its elongated narrow configuration as shown in FIG. 25. The practitioner expands the inverting member 151 to its cup configuration, shown in FIG. 25C, by pressing the releasor lever 218. Next, the practitioner applies upward (proximally directed) tension to the device to seal the rim of the inverting member 151 to the inner wall 181 of the aorta as illustrated in FIGS. 25C and 25D.

The practitioner detaches the hole puncher 178 from the inverter control handle 180 (preferably by unscrewing the hole puncher 178) and sliding the hole puncher 178 own the extrusion 160. Then, the practitioner inserts the head 166 of the hole puncher 178 into the incision 82. This is shown in FIG. 25D. Alternatively, the hole punch head. 166 may be inserted simultaneously with the inverting member 151. The angled distal surface of the hole punch head 166 allows it to penetrate the incision 82 smoothly. Because of the slit-shape of the slit 82 and the natural resiliency of the surrounding aorta wall tissue, the aorta walls 81 close in around the distal portion of the hole punch shaft 182.

Using the outer handle finger grips 174 as a brace, the practitioner pushes the inner handle finger grips 176 toward the outer handle finger grips 174. This compressing motion causes the hole punch enforcer 188 to extend toward the hole punch head 166 until the aorta wall is caught between the hole punch enforcer 188 and the hole punch head 166. This is shown in FIG. 25E. When the practitioner continues to press, the hole punch enforcer 188 punches a circular hole around the incision 82 in the aorta wall 81. The interior surface 186 of the hole punch head 166 pulls the discarded aorta wall tissue into the hole punch aperture 172 and into the hollow interior of the inner handle 168. The practitioner then withdraws the hole puncher 178. When the practitioner releases the inner handle finger grips 176 and outer handle finger grips 174, the hole punch spring 162 causes the hole puncher 178 to return to its starting position. This allows the practitioner to remove the discarded aorta wall tissue from the hole punch head 166.

Once the incision 82 is sufficiently widened by the hole puncher 178, the medical practitioner loosely sutures one end of a coronary artery bypass graft 226 to the aortic tissue surrounding the hole 82. This is shown in FIGS. 26A–28. The end
222 of the bypass graft 226 is preferably cut at an angle to facilitate blood flow and removal of the inverting member 151. FIG. 26B shows an alternative method where a small slit is made at the end 222 of the bypass graft to facilitate the removal of the inverting member 151.

With reference to FIGS. 27 and 28, a purse string stitch is preferably used to suture the bypass graft 226 to the aortic tissue surrounding the hole 82. Alternatively, the practitioner may use a parachute suture or an interrupted suture. When the practitioner loosely sutures almost all the way around the end 222 of the coronary artery bypass graft 226 with the inverting member 151 still within the blood vessel, the end 222 of the bypass graft 226 forms the shape of a 'cobra head' 222.

When the suture 238 is in place, the medical practitioner pushes the translatable piston 17 of the inverter control handle 180 into the outer handle 16. This causes the inverting member 151 to invert into its elongated, narrow configuration. The practitioner then removes the inverting member 151 from the aorta, and immediately pulls the ends of the suture 238 tight to bring the edges of the bypass graft 226 to the aorta (FIG. 28).

Although the embodiments described above use inverting members with a circular cross-section (cup-shaped), various other configurations are possible. For example, the inverting member may have a conical, elliptical, saucer, or boat-shaped cross-sectional configuration.

Also, instead of expandable sleeving mesh, the inverting member may comprise another compliant material with ribs or wires, or the expandable sleeving may have ribs or wires in the mesh to give it structure. Wires in the distal inverting portion 114 may be connected to a distal inverter head piece 152 and connected to other wires in a proximal inverting portion 156 with living or mechanical hinges.

Alternatively, the expandable weave of the sleeving mesh may be sufficiently tight (e.g. less than one quarter inch) so that no blood flows through the mesh. In such embodiments, no compliant material coating, such as silicone, is required on the distal inverting portion 114.

Third Embodiment

FIGS. 29–31 illustrate the distal portion of the device in accordance with another embodiment of the present invention. The proximal portion of the device, including the handle, may be constructed according to one of the above-described embodiments.

As depicted in FIG. 29–31, the distal portion of the device comprises a flexible, hollow tube 242 with a plurality of slits 244 formed therein. The slits 244 extend longitudinally along the tube to define a deformable inverting member 151.

The distal end of each slit 244 ends before it reaches the distal end 246 of the hollow tube 242.

As in the embodiments described above, the distal end 246 of the device is attached to a wire or shaft 232 (FIG. 31) which slides within the tube 242. Pulling the distal end 246 of the hollow tube 242 proximally (via the shaft or wire 232) relative to the proximal end 248 of the hollow tube 242 causes the walls 250 of the inverting member 151 to bend at a preformed creases as the walls move radially outward. The walls 250 are preformed such that the inverting member 151 deforms in an umbrella-like manner to form a cup or saucer-shaped configuration (FIG. 31). The walls 250 of the inverting member 151 may be formed from a material that has a considerably lower elasticity that the materials used for the inverting members of the above-described embodiments.

The deformable inverting member 151 is preferably coated on the exterior with a flexible, impermeable material (not shown) such as silicone rubber to prevent blood from flowing through the incision 82 after the device has been deployed. The device may additionally or alternatively include a stopper (not shown) inside the hollow tube 242 to prevent blood from flowing up from the blood vessel through the hollow tube 242.

As with the embodiments described above, the device includes an actuator assembly (not shown) for allowing the practitioner to remotely control the configuration of the inverting member 151 via the handle. The device can optionally be constructed with a hole puncher (not shown) of the type described above.

The use and operation of this device will now be described with further reference to FIGS. 29–31. The operator inserts the inverting member 151 into the incision 82 made in the blood vessel wall 81. The operator then manipulates the handle in same general manner as described above to apply a compressive force to the inverting member 151. This causes the walls 250 of the inverting member 151 to expand outward away from the center of the hollow tube 242, and to then fold or pivot proximally to form a cup or saucer-shaped configuration. Because the slits are covered by a flexible, impermeable material (not shown), the walls 250 of inverting member 151 form a seal against the inner surface of the vessel wall 81 when the device is pulled distally.

The remaining steps of the procedure are preferably the same as in the embodiments described above.

It will be appreciated from the foregoing that other types of deformable, flexible members can be used to form the cup within the artery, including flexible members that do not invert. For example, a flexible member which opens and closes like an umbrella (without inverting) could be used.

While certain preferred embodiments and particular applications of this invention have been shown and described, it will be apparent to those skilled in the art that various modifications can be made to these designs without departing from the scope of the invention. It is, therefore, to be understood that, within the scope of the appended claims, this invention may be practiced otherwise than as specifically described above.

What is claimed is:

1. A device for forming an anastomosis site along a wall of a blood vessel, comprising:
   an elongate member having a flexible member at a distal end thereof, said flexible member deformable between (i) a narrow configuration in which said flexible member is adapted to be advanced through an incision in a blood vessel, and (ii) an expanded, cup-shaped configuration in which said flexible member is adapted to seal around the incision and thereby form a pocket in which no blood flows; and
   a hole punch device which is slidably deployable along said elongate member, said hole punch device configured to punch an anastomosis hole in the wall of the blood vessel while said flexible member is positioned within the blood vessel and forming said pocket.

2. The device of claim 1, further comprising a handle that is coupled to the elongate member and is releasably attached to said hole punch device.

3. The device of claim 1, said hole punch device comprising:
   a punching member for contacting the vessel and punching the anastomosis hole;
   an outer handle; and
   an inner handle that is movable within said outer handle, wherein said punching member is operably coupled to at least one of said outer handle and said inner handle.

4. The device of claim 3, wherein said punching member includes a hole punch head that engages tissue, so that the tissue punched out from the hole is forced inside one of said outer handle and said inner handle.

5. The device of claim 3, further comprising a spring that operably couples said inner handle with said outer handle, said spring residing within said inner handle and exerting pressure on said inner handle in a proximal direction away from said outer handle to keep said inner handle extended.

6. The device of claim 1, wherein said flexible member is sized to operate within an aortic vessel.

7. The device of claim 1, wherein said flexible member comprises a tubular member.

8. The device as in claim 7, wherein a proximal end of said tubular member is attached to a distal end of said elongate member, and a distal end of the tubular member is attached to a shaft which is slidably mounded within a lumen of said elongate member.

9. The device as in claim 8, wherein said tubular member is preformed to assume an inverted configuration.

10. A method of forming an anastomosis site along the wall of a blood vessel, comprising:
    advancing a flexible member through an incision in a wall of the blood vessel, the flexible member operably coupled to an elongate member;
    causing the flexible member to form a cup having a rim within the blood vessel;
    forming a seal with the cup against an inner surface of the blood vessel wall to thereby form a pocket in which no blood flows;
    sliding a hole punch device along the elongate member; and
    punching an anastomosis hole around the incision with the hole punch device.

11. The method of claim 10, comprising releasing the hole punch device from a handle which is coupled to the elongate member.

12. The method of claim 10, said punching comprising using a punching member to force a section of the wall away from the vessel to create a hole in the vessel.

13. The method of claim 12, comprising punching a circular hole in the vessel.

14. The method of claim 12, comprising pushing the section into the hole punch device.

15. A method of forming an anastomosis site along the wall of a blood vessel, comprising:
    advancing a flexible member through an incision in a wall of the blood vessel, the flexible member operably coupled to an elongate member;
    causing the flexible member to form a cup having a rim within the blood vessel;
    forming a seal with the cup against an inner surface of the blood vessel wall to thereby form a pocket in which no blood flows;
    sliding a hole punch device along the elongate member;
    punching an anastomosis hole around the incision with the hole punch device, said punching comprising using a punching member to force a section of the wall away from the vessel to create a hole in the vessel;
    pushing the section into the hole punch device; and
    discarding the section from the hole punch device.

16. The method of claim 10, wherein the flexible member is a tubular, inverting member.

17. A method of forming an anastomosis site alone the wall of a blood vessel, comprising:
    advancing a flexible member through an incision in a wall of the blood vessel, the flexible member operably coupled to an elongate member;
    causing the flexible member to form a cup having a rim within the blood vessel;
    forming a seal with the cup against an inner surface of the blood vessel wall to thereby form a pocket in which no blood flows;
    sliding a hole punch device alone the elongate member; and
    punching an anastomosis hole around the incision with the hole punch device, wherein said punching comprises sliding two handles relative to each other.

18. The method of claim 17, wherein the handles include an inner handle and an outer handle.

19. The method of claim 17, wherein the wall is pinched between the handles as the handles move relative to each other, thereby punching a section of the wall to form the hole.

20. A method of forming an anastomosis site along the wall of a blood vessel, comprising:
   advancing a flexible member through an incision in a wall of the blood vessel, the flexible member operably coupled to an elongate member;
   causing the flexible member to form a cup having a rim within the blood vessel;
   forming a seal with the cup against an inner surface of the blood vessel wall to thereby form a pocket in which no blood flows;
   sliding a hole punch device along the elongate member; and
   punching an anastomosis hole around the incision with the hole punch device, wherein the cup is formed by moving the elongate member with respect to a second elongate member that is slidably mounted with respect to the first elongate member.

21. The method of claim 20, wherein at least one of the elongate members is withdrawn proximally to cause the rim to form.

22. A method of forming, an anastomosis site along the wall of a blood vessel, comprising:
   advancing a flexible member through an incision in a wall of the blood vessel, the flexible member operably coupled to an elongate member;
   causing the flexible member to form a cup having a rim within the blood vessel;
   forming a seal with the cup against an inner surface of the blood vessel wall to thereby form a pocket in which no blood flows;
   sliding a hole punch device along the elongate member; and
   punching an anastomosis hole around the incision with the hole punch device, wherein the vessel is an aortic vessel.

23. A method of forming an anastomosis site along the wall of a blood vessel, comprising:
   advancing a flexible member through an incision in a wall of the blood vessel, the flexible member operably coupled to an elongate member;
   causing the flexible member to form a cup having a rim within the blood vessel;
   forming a seal with the cup against an inner surface of the blood vessel wall to thereby form a pocket in which no blood flows;
   sliding a hole punch device along the elongate member;
   punching an anastomosis hole around the incision with the hole punch device; and
   loosely suturing one end of a bypass graft to the blood vessel around the hole, with the flexible member positioned within the blood vessel.

24. The method of claim 23, further comprising:
   cutting a short slit at an end of the bypass graft;
   loosely suturing edges of the bypass graft to the blood vessel wall surrounding the hole but leaving the slit at the end of the bypass graft open to remove the flexible member; and
   removing the flexible member from the blood vessel through the slit.

25. A device for forming an anastomosis hole in a vessel wall, comprising:
   a first elongate member;
   a second elongate member;
   a flexible member coupled to said first and second elongate members such that said flexible member is adjustable by relative movement of said elongate members into a configuration in which a rim of said flexible member forms a seal against an inner wall of the blood vessel and a central portion of said flexible member provides a cavity to form a working region within the vessel in which blood does not flow; and
   a hole punch device that is movable along at least one of said elongate members, said hole punch device configured to remove tissue from said vessel wall to provide a hole at a location in the blood vessel where the working region is formed.

26. The device of claim 25, in which said hole punch device is slidable along at least one of said elongate members.

27. The device of claim 25, wherein said first elongate member has a lumen therein, and said second elongate member is slidably received within said first elongate member.

28. The device of claim 25, comprising means for translating one of said elongate members proximally and distally relative to the other of said elongate members to cause said flexible member to change configurations between an elongated, narrow configuration and an inverted configuration.

29. The device of claim 25, wherein said hole punch device includes two handles, said hole punch device forming a hole in the vessel when one of said handles is moved longitudinally with respect to the other of said handles.

30. The device of claim 25, wherein said hole punch device forces wall tissue from the vessel into said hole punch device as the hole is formed.

31. The device of claim 25, wherein said hole punch device is configured to form a circular hole in the vessel.

32. The device of claim 25, further comprising a handle to which said hole punch device is releasably attached.

* * * * *

UNITED STATES PATENT AND TRADEMARK OFFICE
CERTIFICATE OF CORRECTION

PATENT NO.      : 6,171,319 B1                                             Page 1 of 1
DATED           : January 9, 2001
INVENTOR(S)     : Nobles et al.

It is certified that error appears in the above-identified patent and that said Letters Patent is hereby corrected as shown below:

<u>Column 14,</u>
Line 61, please change "alone" to -- along --.

Signed and Sealed this

Twenty-eighth Day of October, 2003

JAMES E. ROGAN
*Director of the United States Patent and Trademark Office*